Nov. 16, 1965 S. J. SAMUELS Plant Pat. 2,570
ROSE PLANT
Filed March 12, 1964
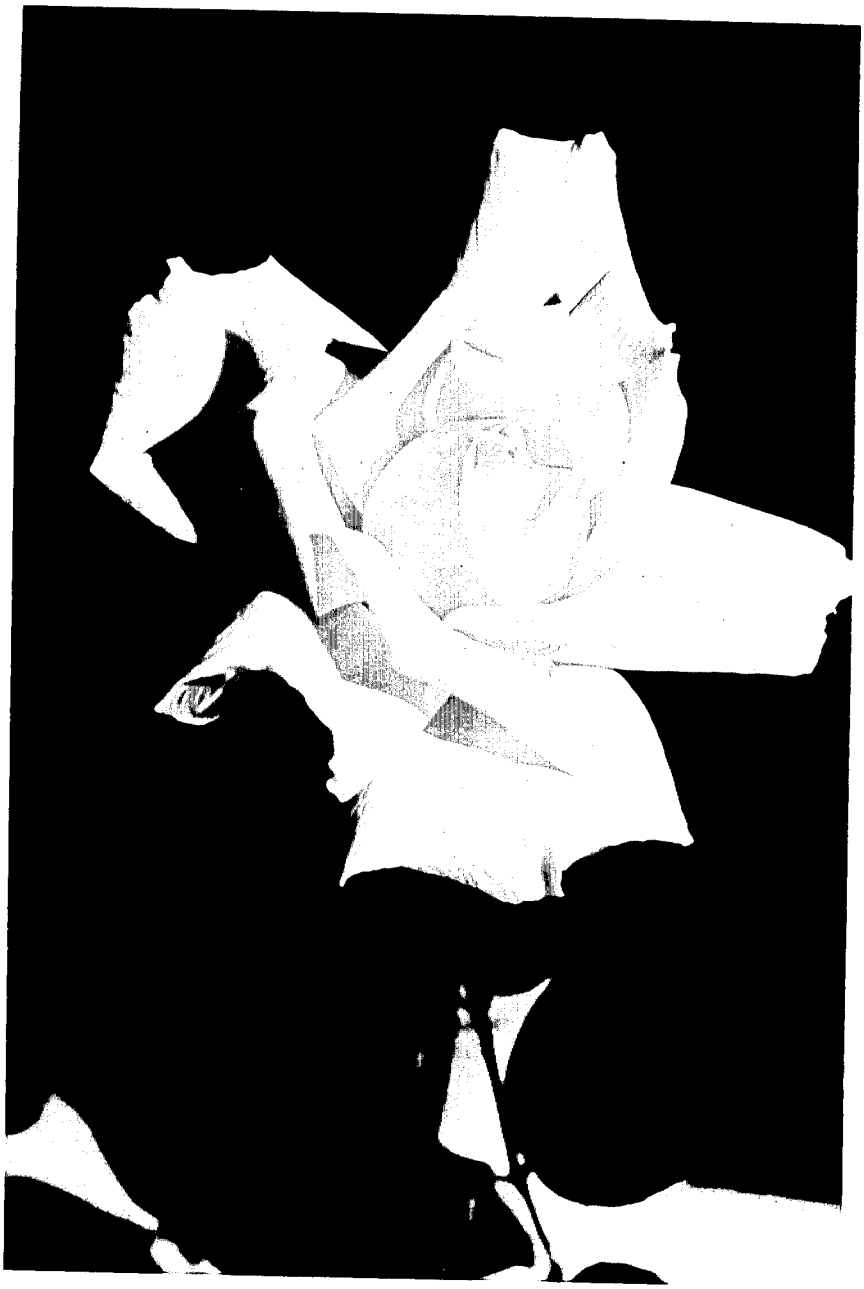
Inventor
Stephen J. Samuels
By
Wenderoth, Lind & Ponack
Attorneys United States Patent Office Plant Pat. 2,570
Patented Nov. 16, 1965

2,570
ROSE PLANT
Stephen J. Samuels, P.O. Box 230,
Nelson, New Zealand
Filed Mar. 12, 1964, Ser. No. 351,576
1 Claim. (Cl. Plt.—18)

The present invention relates to a new and distinct variety of rose plant which was discovered by me as a sport of the variety named "Prima Ballerina" (unpatened), the discovery having been made by me in my cultivated rose nursery located in Nelson, New Zealand. During the normal cultivation of the roses in my nursery, my attention was attracted to one plant amongst the "Prima Ballerina" rose plants, which differed from the bloom of the "Prima Ballerina" in the approximately half of the number of its petals were the same color as the dark pink of "Prima Ballerina" and the remaining number of petals were a much lighter pink. In other words, the petals were not bi-colored in that the dark pink shade was on one face of the petal and the lighter pink shade on the other face of the petal, but in fact the flower carried the dark pink shade and lighter pink shade in separate petals. The foliage and stems were also of a distinctive lighter color compared with the parent as described thereinafter.

Upon close examintation of this particular plant, I found that it had sported and I thereupon took steps to separate the light pink characteristic from the darker pink, and to preserve the light pink sport, keep it under close obseravtion and to later asexually reproduce the same. My observations of the light pink sport and of the asexually reproduced progeny thereof fully confined the distinctions between the sport and its parent, "Prima Ballerina" as well as from all other varieties of which I am aware, as evidenced by the following unique combination of outstanding characteristics which I am convinced represent a new and distinct and commercially important combination in roses of the pink colour range:

(1) Clean, healthy and abundant foliage of large size and leathery texture;

(2) Upright plants with sturdy canes and branches that give the plant a well-clothed appearance;

(3) High resistance to black spot, powdery mildew and rose rust;

(4) Petals of heavy substance and distinctive and attractive colouring and of exceptionally good finishing quality in that spend petals drop off cleanly;

(5) Its profuse flowering and very strong damask fragrance.

Asexual reproduction of my new variety by budding onto root stocks as performed by me in Nelson, New Zealand, shows that the foregoing characteristics and distinctions come true to form and are established and transmitted through succeeding propagations, which establishment and successful propagation has been rigorously tested.

The accompanying drawing shows a typical specimen of the flower and foliage of my new variety as depicted in colour as nearly true as it is reasonably possible to make the same in a colour illustration of this character.

The following is a detailed description of my new variety, with colour terminology in accordance with the Horticultural Colour Chart issued by the British Colour Council except where general colour terms of ordinary dictionary significance are obvious.

Type: Hardy; bush; both greenhouse and outdoor; sport; for cut flowers and for garden decoration.

Class: Hybrid tea.

Parentage: Sport of "Prima Ballerina."

Propagation: Holds it distinguishing characteristics through succeeding propagations by budding onto root stocks.

Flower:

*Locality where grown and observed.*—Nelson, New Zealand.

*Continuity.*—Continuous.

*Fragrance.*—Very strong (damask).

*Flowers borne.*—Singly on long strong stems.

*Quantity of Bloom.*—Profuse, both outdoors and in greenhouse.

Bud:

*Peduncle.*—Medium length, medium weight, erect, stiff, smooth texture with a few tiny reddish-brown prickles. Colour—light bronzy green.

*Before calyx breaks.*—Size—large. Form—long and pointed and without foliaceous appendages on the surface of the bud; without foliaceous parts extending up beyond the tip of the bud. Colour—light bronzy green.

*As calyx breaks.*—Colour— phlox pink, Plate 625/2.

*As first petal opens.*—Form—pointed. Colour outside—phlox pink, Plate 625/2 lightening towards the base. Colour inside—phlox pink, Plate 625/2; canary yellow, Plate 2/2 at base of petals.

*Opening.*—Opens up well; is retarded by cold weather and accelerated by heat.

Bloom:

*Size (when fully open).*—Large, and average size when fully expanded—from 5 to 6 inches.

*Petalage.*—Double; from 28 to 32 petals; arranged regularly.

*Form.*—Full and high-centered at first but becoming open and flattish later; petals at first being loosely rolled outwards, and at maturity remaining rolled outwards, showing stamens.

Petals:

*Texture.*—Thick.

*Appearace.*—Inside—satiny. Outside—satiny.

*Shape.*—Outside—essentially shield - shaped with curved outer end. Intermediate—essentially shield-shaped with curved outer end. Inside—essentially shield-shaped with curved outer end.

This description of a newly opened flower was made from a rose grown outdoors during the month of February in Nelson, New Zealand.

*Colour.*—Outer petal: outside surface—phlox pink, Plate 625/2 lightening towards base; inside surface—phlox pink, Plate 625/2. Intermediate petal: outside surface—phlox pink, Plate 625/2; inside surface—phlox pink, Plate 625/2. Inner petal: outside surface—phlox pink, Plate 625/2; inner surface—phlox pink, Plate 625/2. Base of all petals inside and outside surfaces—canary yellow, Plate 2/2.

This description was made from a rose that was open for three days during the month of February at Nelson, New Zealand.

*Colour.*—Outer petal: outside surface—rose pink, Plate 427/2; inside surface—rose pink, Plate 427/3. Intermediate petal: outside surface—rose pink, Plate 427/3; inside surface—rose pink, Plate 427/3. Inner petal: outside surface—rose pink, Plate 427/3; inside surface—rose pink, Plate 427/3. Base of all petals remain canary yellow, Plate 2/2.

*General colour effect.*—Newly opened flower—light bright pink. Three days open—slightly lighter.

*Behaviour.*—Persist—fading slightly from phlox pink to rose pink. Spent petals drop off cleanly.

*Flower longevity.*—On bush in garden—5 days in February in New Zealand. Cut flowers grown outdoors and kept at living room temperatures—5 days in February in New Zealand. Greenhouse grown cut flowers in living room temperatures—5 days in February in New Zealand.

Reproductive organs:

*Stamens.*—Many; regularly arranged about pistils.

*Filaments.*—Medium length, many; with anthers, Colour—reddish.

*Anthers.*—Medium size, open all at once. Colour—gold.

*Pollen.*—Moderate abundance. Colour—Saffron yellow, Plate 7/1.

*Pistils.*—Many.

*Styles.*—Even; medium length; very compactly bunched. Colour—reddish.

*Stigma.*—Colour—pinkish yellow.

*Ovaries.*—All enclosed in calyx.

*Hips.*—Spherical shaped; thick walls. Colour—from green to mahogany with whitish bloom that gives purplish appearance.

*Sepals.*—Permanent; long; slender; pointed. Colour—from green to brown.

*Seeds.*—Few; average approximately ten in number; large size.

Plant:

*Leaves.*—Compound of 5 leaflets; abundant; large size; heavy; leathery, bright appearance.

*Leaflets.*—Shape—oval. Base—round. Tip—pointed. Margin—serrated.

*Colour.*—Mature upper surface—spinach green, Plate 0960, under surface—spinach green, Plate 0960/3. Young: upper surface—bronze green; under surface—purplish bronze.

*Rachis (the supporting stem of the compound leaf).*—Heavy; upper side—grooved; under side—moderately thorny.

*Stipules.*—Medium length; wide; with medium points at angle of approximately 45°.

*Disease resistance.*—Very good resistance to diseases, as determined by comparison with other varieties grown under comparable cultural conditions at Nelson, New Zealand.

Growth:

*Habit.*—Upright.

*Growth.*—Vigorous.

*Canes.*—Heavy.

*Main stems.*—Colour—light green. Thorns—moderate number; medium length; hooked downwards about 80°, with long narrow base; brownish. Prickles—few; brown. Hairs—none.

*Branches.*—Colour—pale green. Thorns—moderate number; medium length; hooked downwards about 80°. Prickles—few; colour—brownish. Hairs—none.

*New shoots.*—Colour—bronzy green. Thorns—moderate number medium length; hooked downwards about 80°. Hairs—none.

| Foliage Color | Parent "Prima Ballerina" | Sport |
|---|---|---|
| Mature Leaf: | | |
| Upper surface | Parsley green 00962 | Spinach green 0960. |
| Under surface | A little darker than spinach green 0960/3. | Spinach green 0960/3. |
| Young Leaf: | | |
| Upper | Bronzy | Bronze green. |
| Under | Slightly deeper than the claimed variety. | |
| Stem Color: | | |
| Main Stem | Parsley green with bronzy tints. | Light green. |
| Branches | Medium green | Pale green. |
| New Shoots | Light bronzy green | Bronzy green. |

| Petal Colors newly opened bloom | Parent "Prima Ballerina" | Sport |
|---|---|---|
| As calyx breaks | Rose red 724/2 | Phlox pink 625/2. |
| As first petal opens (outside). | Rose red 724/2 | Phlox pink lightening towards base. |
| As first petal opens (inside). | Rose red 724 | Phlox pink 625/2. |
| Color at base | Canary yellow 2/2 | Canary yellow 2/2. |
| Newly opened Flower: | | |
| Outer petal— | | |
| Outside | Deep pink | Phlox pink 625/2 lightening toward base. |
| Inside | do | Phlox pink 625/2. |
| Intermediate— | | |
| Outside | do | Do. |
| Inside | do | Do. |
| Inner petal— | | |
| Outside | do | Do. |
| Inside | do | Do. |
| Base of all petals inside and outside surfaces on both are canary yellow 2/2 | | |
| Open 3 days: | | |
| Outer petal— | | |
| Outside | Rhodamine Pink 527 | Rose pink 427/2. |
| Inside | do | Rose pink 427/3. |
| Intermediate— | | |
| Outside | do | Do. |
| Inside | do | Do. |
| Inner petal— | | |
| Outside | do | Do. |
| Inside | do | Do. |
| All petals lighten towards base. Base of all petals remain on both canary yellow 2/2 | | |
| General Color Effect: | | |
| Newly opened | Deep pink | Light bright pink. |
| 3 days open | Slightly lighter | Slightly lighter. |

What I do claim and desire to obtain by Letters Patent of the United States of America is:

A new and distinct variety of rose plant of the hybrid tea class, substantially as herein shown and described, characterised particularly, as to novelty by the unique combination of abundant, clean, healthy foliage of large size and leathery texture on vigorous, upright plants, with study canes and branches that give the plant a well-clothed appearance, its high resistance to black spot, powdery mildew and rose rust; petals of heavy substance and distinctive and attractive colouring and of exceptionally good finishing quality in that spend petals drop off cleanly; by its profuse flowering and its very strong demask fragrance.

No references cited.

ABRAHAM G. STONE, *Primary Examiner.*